United States Patent
Yamamoto et al.

(10) Patent No.: US 8,591,828 B2
(45) Date of Patent: Nov. 26, 2013

(54) HYDROGEN GAS DETECTING MEMBRANE

(75) Inventors: Shunya Yamamoto, Takasaki (JP);
Katsuyoshi Takano, Takasaki (JP);
Aichi Inouye, Takasaki (JP); Masahito Yoshikawa, Takasaki (JP)

(73) Assignee: Japan Atomic Energy Agency, Ibaraki (JP)

( * ) Notice: Subject to any disclaimer, the term of this patent is extended or adjusted under 35 U.S.C. 154(b) by 957 days.

(21) Appl. No.: 12/153,144

(22) Filed: May 14, 2008

(65) Prior Publication Data
US 2008/0283388 A1    Nov. 20, 2008

(30) Foreign Application Priority Data
May 15, 2007   (JP) .................................. 2007/129338

(51) Int. Cl.
*G01N 21/00*    (2006.01)

(52) U.S. Cl.
USPC ............ 422/425; 422/63; 422/82.05; 422/83; 422/88

(58) Field of Classification Search
USPC .............................. 422/425, 63, 82.05, 83, 88
See application file for complete search history.

(56) References Cited

U.S. PATENT DOCUMENTS

| | | | | |
|---|---|---|---|---|
| 4,661,320 A | * | 4/1987 | Ito et al. | 422/86 |
| 4,892,834 A | * | 1/1990 | Rauh | 436/149 |

FOREIGN PATENT DOCUMENTS

| | | |
|---|---|---|
| JP | 60-39536 | 3/1985 |
| JP | 8-253742 | 10/1996 |
| JP | 2005-345338 | 12/2005 |

OTHER PUBLICATIONS

Ishiji et al. "Amperometric Carbon Dioxide Gas Sensor Based on Electrode Reduction of Platinum Oxide", Anal. Chem., 1983, 65, 2736-2739.*

K. Ito, et al. "Hydrogen detection based on coloration of anodic tungsten oxide film", Oct. 22, 1991, pp. 938-940.

* cited by examiner

*Primary Examiner* — Monique Cole

(57) ABSTRACT

An optical hydrogen gas detecting membrane is prepared by sequentially depositing a platinum oxide layer and a catalytic metal layer on a transparent substrate, such as quartz glass, by vapor deposition such as the sputtering method. Palladium or platinum is used as the catalytic metal layer.

4 Claims, 3 Drawing Sheets

3 CATALYTIC METAL LAYER
2 PLATINUM OXIDE LAYER
1 TRANSPARENT SUBSTRATE

HYDROGEN GAS DETECTING MEMBRANE

BACKGROUND OF THE INVENTION

1. Field of the Invention

This invention relates to an optical hydrogen gas detecting membrane which detects a hydrogen gas by measuring a change in the transmittance of light when exposed to an atmosphere containing hydrogen, the hydrogen gas detecting membrane using a thin film of platinum oxide.

2. Description of the Related Art

In recent years, global warming due to the emission of greenhouse gases ($CO_2$, etc.) associated with mass consumption of fossil fuels has posed a problem. In response, the realization of an energy supply system relying minimally on fossil fuels has been necessitated. A system for electric power supply by a hydrogen fuel cell, in particular, is an electric power supply system which does not discharge $CO_2$ as a greenhouse gas. Technologies for its construction are under study in many fields as an infrastructure for realizing hydrogen society aimed at sustained development.

However, hydrogen as a fuel is a combustible gas involving explosion, and its handling requires a careful safety measure. For this purpose, the development of a gas sensor or a gas detecting membrane, which safely detects a leaking trace hydrogen gas, becomes one of the most important challenges in realizing hydrogen society. Hydrogen sensors, which have been put to practical use, measure a change in electrical resistance on the surface of a semiconductor due to the adsorption of hydrogen to detect hydrogen. Since they embrace a power circuit which can become an ignition source for explosion, however, they have been problematic in terms of safety.

As a hydrogen detecting method which does not need a power circuit as a possible ignition source for explosion, there is a method using a hydrogen gas detecting adhesive tape comprising titanium oxide coated with a palladium oxide hydrate which is colored upon exposure to a hydrogen gas (see JP-A-8-253742). This tape has been proposed as a hydrogen detecting material capable of visual confirmation. However, it presents the problem that under ultraviolet radiation in an outdoor setting or the like, its sensitivity to detect a hydrogen gas declines because of the photocatalytic effect of titanium oxide.

Proposals have also been made for a hydrogen gas detecting tape using a hydrogen gas detecting coating pigment consisting essentially of fine tungsten oxide particles which are colored upon exposure to a hydrogen gas (see JP-A-2005-345338); and for optically detecting hydrogen sensors measuring the transmittance of light by a tungsten trioxide film, which is colored with a hydrogen gas, with the use of laser, a light emitting diode (LED) light source, and an optical detector such as a photodiode, in order to detect a hydrogen gas with high sensitivity (see JP-A-60-39536 and K. Ito and T. Ohgami, Appl. Phys. Lett. 60 (1992) 938).

A thin film of a metal oxide, such as tungsten trioxide, having palladium deposited thereon as a catalytic metal for dissociating a hydrogen molecule adsorbed to the surface into a hydrogen atom has the property of decreasing in the transmittance of light when touching an atmosphere containing hydrogen. Thus, it is the most promising candidate for a next-generation hydrogen detecting material.

To form a tungsten trioxide film which changes in optical characteristics in the presence of hydrogen, as described above, it is necessary to exercise subtle compositional control, such as the introduction of oxygen defects into tungsten trioxide, or crystal structure control such as amorphization. However, it has not been easy to form, with satisfactory reproducibility, tungsten oxide whose optical characteristics promptly change in response to a hydrogen gas. Thus, there has been a demand for a hydrogen detecting material which, when prepared, does not require control over the amount of oxygen defects.

The present invention has been accomplished in the light of the above-described circumstances. It is an object of the invention to provide a hydrogen gas detecting membrane whose safety is not problematic, whose manufacturing method is simple, and which can be prepared with satisfactory reproducibility.

SUMMARY OF THE INVENTION

The inventors have focused attention on platinum oxide, which has not been proposed as a hydrogen detecting material, in connection with an optical hydrogen gas detecting membrane making use of the property of decreasing in the transmittance of light upon exposure to an atmosphere containing hydrogen. They have found that hydrogen can be detected by depositing a catalytic metal on the surface of the platinum oxide. Based on this finding, they have accomplished the present invention.

An aspect of the present invention is an optical hydrogen gas detecting membrane for detecting a hydrogen gas by measuring a change in the transmittance of light when exposed to an atmosphere containing hydrogen, the hydrogen gas detecting membrane comprising a platinum oxide layer and a catalytic metal layer deposited sequentially on a substrate, the platinum oxide layer being a thin film comprising platinum oxide ($PtO_2$), the catalytic metal layer being adapted to dissociate a hydrogen molecule into a hydrogen atom.

It is preferred that the film thickness of the platinum oxide layer be 10 nm or more, but 1 µm or less.

Preferably, the platinum oxide layer and the catalytic metal layer are prepared using vapor deposition.

Preferably, the catalytic metal layer comprises palladium or platinum, especially palladium.

Preferably, the substrate comprises a substance permeable to light in the visible light region.

According to the present invention, there is provided the hydrogen gas detecting membrane composed of the thin platinum oxide film and the catalytic metal. The layer of the catalytic metal, which is either palladium or platinum, is deposited on the surface of the film of platinum dioxide ($PtO_2$) formed on a transparent substrate. By so doing, there can be provided the hydrogen gas detecting membrane which can detect hydrogen at a hydrogen concentration of not higher than 4%, an explosion limit, in air at room temperature (20° C.), as will be demonstrated by Examples to be offered later.

Moreover, platinum oxide is used as a principal component. Thus, the hydrogen gas detecting membrane can be prepared with satisfactory reproducibility and with convenience by vapor deposition such as the sputtering method. Also, it becomes possible to achieve hydrogen detection without providing a power circuit or the like, as a possible ignition source, in the hydrogen gas detecting portion. Hence, the hydrogen gas detecting membrane is expected to be applied to an optical hydrogen leak detector using an optical fiber.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
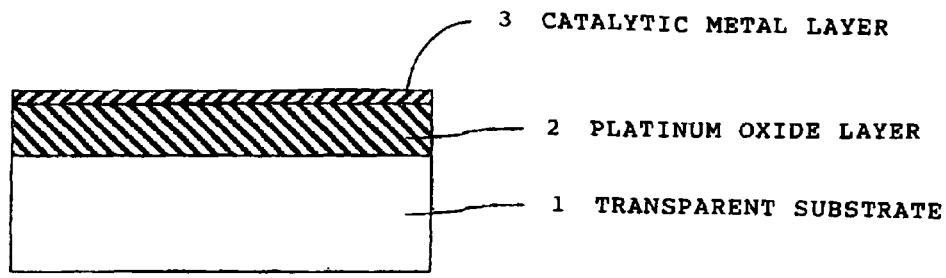
FIG. 1 is a sectional view showing a hydrogen gas detecting membrane according to an embodiment of the present invention.

FIG. 1 shows a sectional view of a hydrogen gas detecting membrane according to an embodiment of the present invention.

This hydrogen gas detecting membrane has a platinum oxide layer 2 and a catalytic metal layer 3 deposited sequentially on a transparent substrate 1 by vapor deposition such as the sputtering method. The side including the catalytic metal layer 3 serves as a hydrogen gas detecting surface.

Transparent Substrate 1:

A substance permeable to light in the visible light region, for example, an oxide such as quartz or sapphire, or an organic material such as polyethylene terephthalate (PET) or polyethylene, can be used as a substrate material on which a thin film of platinum oxide is formed.

Platinum Oxide Layer 2:

The platinum oxide layer 2 used for hydrogen gas detection is of a composition consisting essentially of platinum dioxide ($PtO_2$) and, preferably, is a thin film having a thickness of 1 µm or less. As the platinum oxide layer 2, platinum dioxide ($PtO_2$) is formed on the transparent substrate 1, such as quartz, by use of vapor deposition such as the sputtering method. For example, the formation of the platinum oxide layer 2 is carried out by sputtering a platinum plate in a gas mixture of argon and oxygen by high-frequency magnetron sputtering. However, direct current sputtering, laser ablation, or vacuum evaporation may be employed.

The platinum oxide layer 2, if its film thickness is less than 10 nm, makes it difficult to measure a change in the coloration of the thin platinum oxide film due to hydrogen. Its thickness exceeding 1 µm lowers the permeation of light in the visible light region, making it difficult to measure a change in the transmittance of light due to hydrogen. Thus, the thickness of the platinum oxide layer 2 is preferably 10 nm or more, but 1 µm or less.

Catalytic Metal Layer 3:

The catalytic metal layer 3 can be formed by depositing a catalytic metal, which is palladium or platinum, on the surface of the platinum oxide layer 2 by use of the high frequency sputtering method. Also, direct current sputtering, laser ablation, or vacuum evaporation may be employed.

EXAMPLE 1

A thin platinum oxide film was prepared on the surface of a quartz substrate of 0.5 mm in thickness with the use of high frequency sputtering. In forming the film, a platinum disk with a diameter of 50 mm, a thickness of 1 mm, and purity of 99.99% was used as a target, and the platinum target was sputtered at an electric power of 50 W in an argon-oxygen mixed gas (0.315 Pa) atmosphere having an argon gas partial pressure of 0.155 Pa and an oxygen gas partial pressure of 0.160 mPa, to perform platinum oxide film formation on the quartz substrate at room temperature (20° C.). The thickness of the platinum oxide film was about 296 nm in a film formation time of 10 minutes.

On this thin platinum oxide film, palladium as a catalyst was deposited in a thickness of about 15 nm by use of the high frequency sputtering method. For the sputtering of palladium, a metallic palladium disk with a diameter of 50 mm, a thickness of 5 mm and purity of 99.99% was used as a target, and film formation was carried out for 40 seconds under the conditions involving an electric power of 50 W and an argon gas pressure of 0.185 Pa.

The crystal structure and composition of the resulting platinum oxide film were evaluated using the X-ray diffraction method and Rutherford backscattering spectroscopy. The resulting platinum oxide was found to be amorphous platinum dioxide ($PtO_2$).

Figure 2:
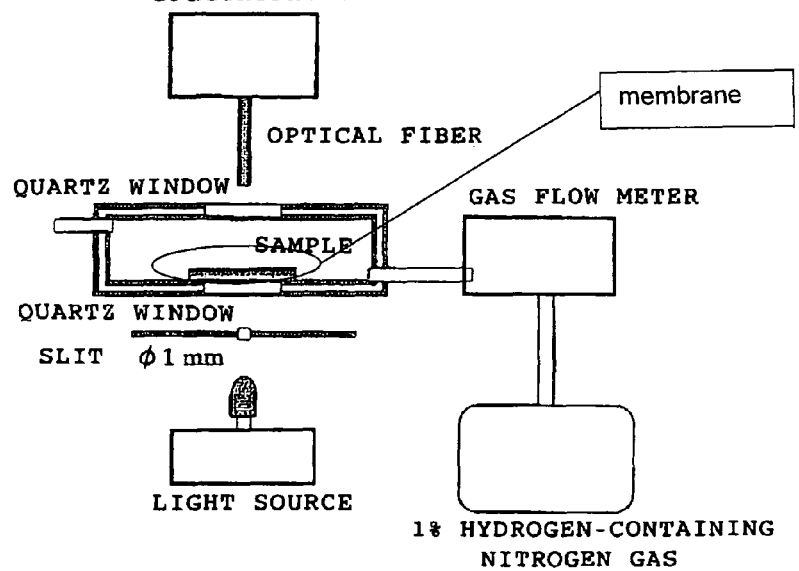
FIG. 2 is a schematic view showing an apparatus for measuring a change in the transmittance of light in response to hydrogen.

Changes in the optical characteristics responsive to a hydrogen gas were evaluated at room temperature (20° C.) using a measuring device shown in FIG. 2. The hydrogen gas used in the evaluation was hydrogen at a concentration of 1.0% diluted with a nitrogen gas. A sample in a container whose atmosphere can be controlled was irradiated with red light with a wavelength of 645 nm, and measurements were made by the following procedure using a spectrophotometer measuring light via an optical fiber: First, the transmitted light intensity $I_0$ of the sample before exposure to the hydrogen gas was measured. Then, hydrogen at a concentration of 1.0% diluted with nitrogen was introduced into a sample cell at a flow rate of 100 sccm (standard cc/min), and the transmitted light intensity I was measured. Based on the ratio between the transmitted light intensities, $I/I_0$, a change in the transmittance of light due to hydrogen was evaluated.

Figure 3:
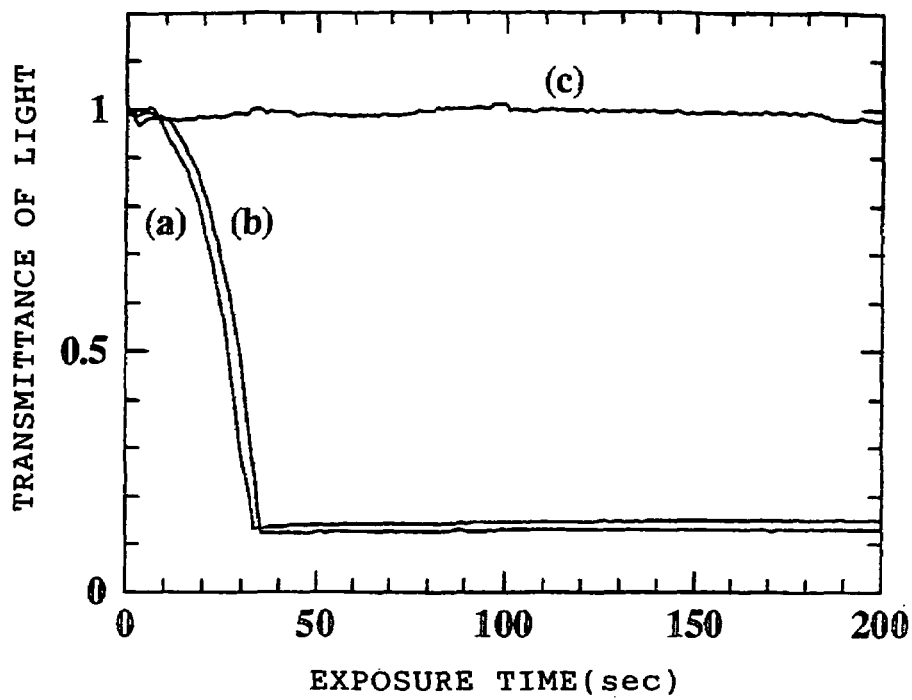
FIG. 3 is a graph showing changes over time in the transmittance of light in the hydrogen gas detecting membrane in response to a 1% hydrogen gas diluted with nitrogen, in which the curve (a) represents the results when a palladium catalyst layer was present (Example 1), the curve (b) represents the results when a platinum catalyst layer was present (Example 2), and the curve (c) represents the results when no catalyst layer was present (Comparative Example 1)

In FIG. 3, the curve (a) represents hydrogen-associated changes over time in the transmittance of light in the hydrogen gas detecting membrane prepared above. As shown by this curve, with the increase in the time of exposure to the hydrogen gas, the transmittance of light sharply decreased, showing a change in the transmittance of the order of 87% in 30 seconds. This finding shows that the hydrogen gas detecting membrane prepare in the above manner has the ability to sufficiently detect a hydrogen gas at an explosion limit concentration (about 4%) or lower.

EXAMPLE 2

Platinum was deposited in a thickness of about 15 nm at room temperature (20° C.) on a thin platinum oxide film prepared on a quartz substrate in the same manner as in Example 1. Changes over time in the transmittance of light due to hydrogen were measured as in Example 1. The results of the measurements are shown by the curve (b) in FIG. 3.

It can be confirmed that with the platinum oxide film having platinum deposited thereon, as the time of exposure to the hydrogen gas increased, the transmittance of light decreased. This outcome shows that even when platinum is used as the catalytic metal, coloration of the platinum oxide layer occurs in response to the hydrogen gas, indicating that the hydrogen gas is detectable.

Comparative Example 1:

As a comparison for Examples 1 and 2, a sample was produced by preparing a thin platinum oxide film under the same conditions as in Example 1, but without depositing a catalytic metal. This sample was evaluated for changes over time in the transmittance of light due to hydrogen.

As shown by the curve (c) in FIG. 3, with the platinum oxide having no catalytic metal deposited thereon, the transmittance of light remained unchanged in response to hydrogen up to 200 seconds after start of exposure to hydrogen. Based on this finding, when a hydrogen gas is detected using a platinum oxide film, it is important to deposit a catalytic metal on the platinum oxide film.

EXAMPLE 3

Using sapphire, polyethylene, and polyethylene terephthalate (PET) as substrate materials, thin platinum oxide films were prepared under the same conditions as in Example 1. These platinum oxide films were measured for changes over time in the transmittance of light due to hydrogen as in Example 1. On each platinum oxide film, palladium was deposited as a catalytic metal in a thickness of about 15 nm.

Figure 4:
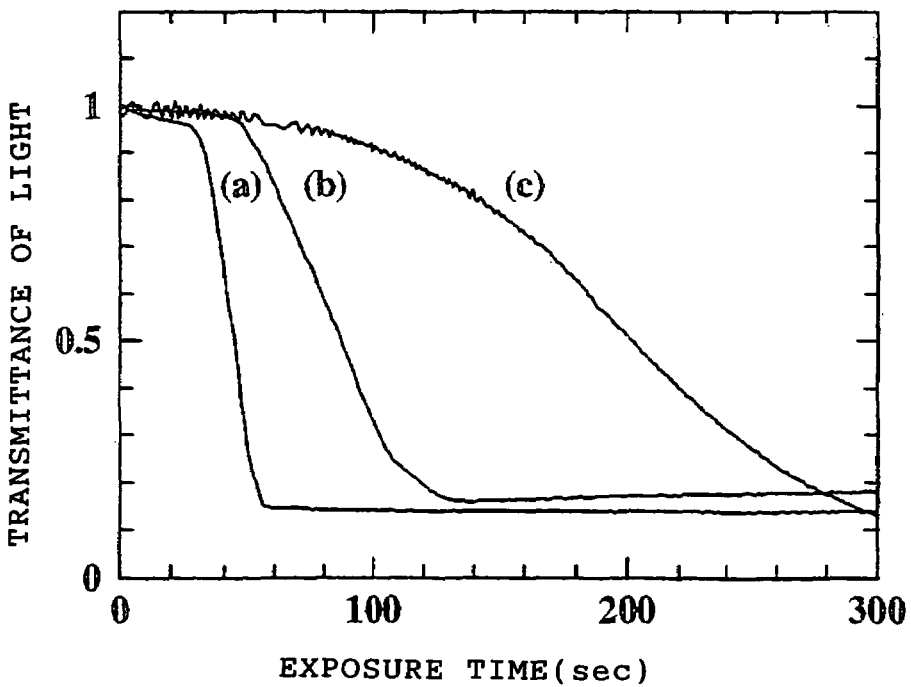
FIG. 4 is a graph showing changes over time in the transmittance of light in the hydrogen gas detecting membrane in response to a 1% hydrogen gas diluted with nitrogen (Example 3), in which the curve (a) represents the results when a sapphire substrate was used, the curve (b) represents the results when a polyethylene substrate was used, and the curve (c) represents the results when a polyethylene terephthalate (PET) substrate was used.

Curves (a), (b) and (c) in FIG. 4 show the results of measurements of the platinum oxide films formed on the sapphire substrate, the polyethylene substrate, and the PET substrate, respectively. The platinum oxide films formed on any of the substrates were confirmed to be colored in response to hydrogen. Thus, it can be found that inorganic materials such as sapphire, and polymeric materials such as PET, which allow passage of light in the visible light region, can be utilized as substrates for hydrogen gas detecting membranes.

EXAMPLE 4

Samples were prepared under the same conditions as in Example 1, and evaluated for the ability to detect a 1.0%, 0.5% and 0.1% hydrogen gas diluted with nitrogen. For this purpose, the platinum oxide films were measured for changes over time in the transmittance of light due to hydrogen in the same manner as in Example 1.

Figure 5:
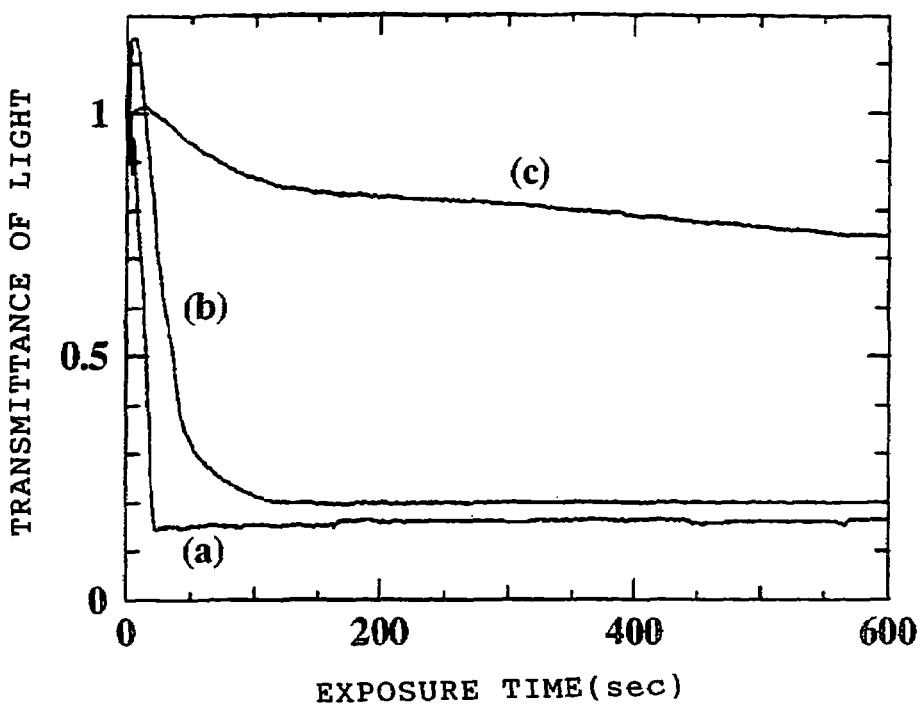
FIG. 5 is a graph showing changes over time in the transmittance of light in the hydrogen gas detecting membrane (palladium was used as a catalytic metal) in response to a (a) 1.0%, (b) 0.5%, and (c) 0.1% hydrogen gas diluted with nitrogen.

FIG. 5 shows changes over time in the transmittance of light in the samples (using palladium as the catalytic metal) in response to a (a) 1.0%, (b) 0.5%, and (c) 0.1% hydrogen gas diluted with nitrogen.

Figure 6:
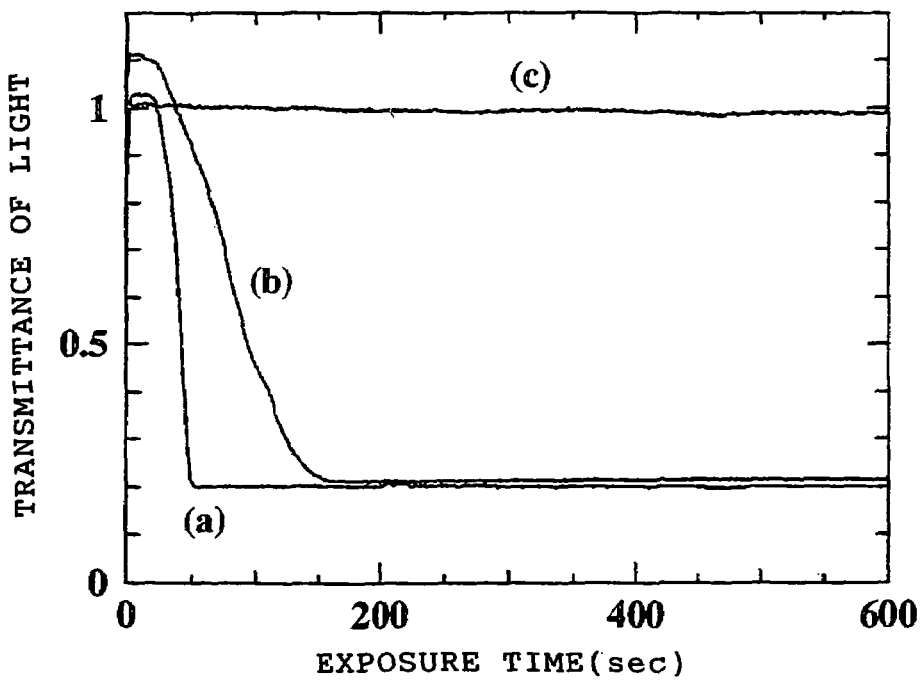
FIG. 6 is a graph showing changes over time in the transmittance of light in the hydrogen gas detecting membrane (platinum was used as a catalytic metal) in response to a (a) 1.0%, (b) 0.5%, and (c) 0.1% hydrogen gas diluted with nitrogen.

FIG. 6 shows changes over time in the transmittance of light in the samples (using platinum as the catalytic metal) in response to a (a) 1.0%, (b) 0.5%, and (c) 0.1% hydrogen gas diluted with nitrogen.

Based on the results of FIG. 5 and FIG. 6, the transmittance of light in any samples changed upon exposure to the 0.5% hydrogen gas, thus confirming the detectability of the hydrogen gas. Hence, the hydrogen gas detecting membranes prepared in Example 4, like that of Example 1, were found to be able to detect hydrogen not higher than the explosion limit (4%) in air at room temperature (20° C.).

In connection with the 0.1% hydrogen gas, only the platinum oxide film using palladium as the catalyst was able to confirm the change in the transmittance of light. Thus, the use of palladium as the catalytic metal was found to be preferred.

The use of the hydrogen gas detecting membrane according to the present invention permits hydrogen detection not involving a power circuit or the like, which becomes an ignition source, in the hydrogen gas detecting portion. This hydrogen gas detecting membrane can be utilized as a portable hydrogen leak detection system using a hydrogen sensor and an optical fiber. Moreover, the present invention is useful for providing an optical hydrogen gas detecting membrane which is indispensable to technologies for commercialization of next-generation hydrogen energy, and which ensures safety.

While the preferred embodiments of the present invention have been described in detail by reference to the accompanying drawings, it is to be understood that the invention is not limited to such embodiments, but various changes and modifications may be made without departing from the scope of the present invention.

What is claimed is:

1. An optical hydrogen gas detecting system using a membrane for detecting a hydrogen gas by measuring a change in transmittance of light when exposed to an atmosphere containing hydrogen, comprising:
   a membrane to detect a hydrogen comprising a platinum oxide layer formed by sputtering in a gas mixture of argon and oxygen and a catalytic metal layer deposited sequentially on a substrate, the platinum oxide layer being a thin film comprising platinum oxide ($PtO_2$), the catalytic metal layer being adapted to dissociate a hydrogen molecule into a hydrogen atom; and
   an optical element to measure transmitted light intensity.

2. The hydrogen gas detecting system according to claim 1, wherein a film thickness of the platinum oxide layer is in the range of 10 nm-1 μm.

3. The hydrogen gas detecting system according to claim 1, wherein the catalytic metal layer is a layer of palladium or platinum.

4. The hydrogen gas detecting system according to claim 1, wherein the substrate comprises a substance permeable to light in a visible light region.

* * * * *